United States Patent
Klotz et al.

(10) Patent No.: US 8,945,138 B2
(45) Date of Patent: Feb. 3, 2015

(54) INSTRUMENT FOR MODULAR ORTHOPAEDIC PROSTHESIS

(75) Inventors: Conrad L. Klotz, Napanee, IN (US); Chad L. Baughman, Columbia City, IN (US); Daniel J. Williman, Warsaw, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 2032 days.

(21) Appl. No.: 11/529,887

(22) Filed: Sep. 29, 2006

(65) Prior Publication Data

US 2008/0161823 A1    Jul. 3, 2008

(51) Int. Cl.
*A61B 17/58*    (2006.01)
*A61F 2/46*    (2006.01)
*A61F 2/40*    (2006.01)

(52) U.S. Cl.
CPC ............ *A61F 2/4684* (2013.01); *A61F 2/4637* (2013.01); *A61F 2/40* (2013.01); *A61F 2/4014* (2013.01); *A61F 2/4059* (2013.01); *A61F 2002/4018* (2013.01); *A61F 2002/4029* (2013.01); *A61F 2002/4037* (2013.01); *A61F 2002/4044* (2013.01); *A61F 2002/4062* (2013.01); *A61F 2002/4668* (2013.01)
USPC ............................................ 606/102; 606/99

(58) Field of Classification Search
USPC ................. 606/102, 306, 916, 99; 623/19.11, 623/19.12, 19.14, 22.11, 18.11, 20.11, 623/20.12, 20.13, 20.22, 23.4; 81/55
See application file for complete search history.

(56) References Cited

U.S. PATENT DOCUMENTS

| | | | |
|---|---|---|---|
| 4,003,095 A * | 1/1977 | Gristina | 623/19.12 |
| 5,370,706 A | 12/1994 | Bolesky et al. | |
| 5,702,457 A | 12/1997 | Walch et al. | |
| 5,741,335 A | 4/1998 | Gerber et al. | |
| 6,139,549 A * | 10/2000 | Keller | 606/86 A |
| 6,203,575 B1 | 3/2001 | Farey | |
| 6,228,120 B1 * | 5/2001 | Leonard et al. | 623/19.12 |
| 6,283,999 B1 | 9/2001 | Rockwood, Jr. | |
| 6,558,425 B2 | 5/2003 | Rockwood, Jr. | |
| 6,620,197 B2 | 9/2003 | Maroney et al. | |
| 6,626,946 B1 * | 9/2003 | Walch et al. | 623/19.11 |

(Continued)

FOREIGN PATENT DOCUMENTS

EP    0 940 126 A1    9/1999
WO    01/82843 A2    11/2001

OTHER PUBLICATIONS

Extended European Search Report corresponding to European Application No. 07253854.9, dated Jan. 24, 2008 (6 pages).

*Primary Examiner* — Christian Sevilla
(74) *Attorney, Agent, or Firm* — Maginot, Moore & Beck LLP

(57) ABSTRACT

A kit for use in performing a trail reduction in joint arthroplasty is provided. The kit includes a trail stem assembly including a first component, a second component selectably moveable with respect to the first component, and a fastener for securing the first component to the second component. The kit also includes an articulating trial component removeably fixedly secured to the trail stem assembly and a driver for cooperation with the fastener to secure the first component to the second component. The kit also includes a handle. The handle has a first feature for permitting the driver to pass through the handle and a second feature for orientably connecting the handle to the articulating trial component.

20 Claims, 16 Drawing Sheets

(56) References Cited

U.S. PATENT DOCUMENTS

| | | |
|---|---|---|
| 6,673,114 B2 | 1/2004 | Hartdegen et al. |
| 6,736,851 B2 | 5/2004 | Maroney et al. |
| 2001/0053935 A1* | 12/2001 | Hartdegen et al. .......... 623/19.12 |
| 2004/0010261 A1* | 1/2004 | Hoag et al. ...................... 606/99 |
| 2004/0064188 A1* | 4/2004 | Ball et al. ................... 623/19.11 |
| 2004/0122440 A1* | 6/2004 | Daniels et al. ................ 606/102 |

* cited by examiner

INSTRUMENT FOR MODULAR ORTHOPAEDIC PROSTHESIS

TECHNICAL FIELD OF THE INVENTION

The present invention relates generally to the field of orthopaedics, and more particularly, to an instrument for use in arthroplasty.

BACKGROUND OF THE INVENTION

The present invention relates to implantable articles and methods of for implanting such articles. More particularly the invention relates to a bone prosthesis, prosthesis trial, instrument and method for implanting the same.

There are known to exist many designs for and methods for implanting implantable articles, such as bone prostheses. Such bone prostheses include components of artificial joints, such as elbows, hips, knees and shoulders.

One such implantable prosthesis is a shoulder prosthesis. During the life time of a patient, it may be necessary to perform a total shoulder replacement procedure on a patient as a result of, for example, disease or trauma, for example disease from osteoarthritis or rheumatoid arthritis. Currently, most implantable shoulder prostheses are total shoulder prostheses. In a total shoulder replacement procedure, a humeral component having a head portion is utilized to replace the natural head portion of the upper arm bone or humerus. The humeral component typically has an elongated intermedullary stem, which is utilized to secure the humeral component to the patient's humerus. In such a total shoulder replacement procedure, the natural glenoid surface of the scapula is resurfaced or otherwise replaced with a glenoid component that provides a bearing surface for the head portion of the humeral component.

In performing arthroplasties, the prosthesis, particularly for humeral prosthesis, have more recently been provided with humeral heads that are adjustable with respect to the stem portion of the prosthesis. Because of this adjustability, a trial head must first be used to determine what the correct position of the final implant should be. Adjusting the position of the trial head on the resected humeral bone may be difficult for at least two reasons. First, there may be a limited space in the surgical site. Such limited space is more of an issue in surgeries that utilize minimally invasive techniques where the incision lengths are somewhat shorter. If a surgeon must manipulate the position of the trial head with his hand, he may no longer have visibility to determine its correct position because his hand may block the view of the resected surface.

Adjusting the trial head is more of a problem for those surgeons who utilize a less invasive technique. Less invasive techniques where the incision length is shorter may not allow for enough space for the surgeon to use his hands to properly position the trial head. An additional issue with adjusting the trial head on the resected humeral bone is that the fluids typically found in the surgical site make the surgeon's latex glove very slippery. Without the use of the trial head handle, surgeons may have to hold onto the trial head with one hand while tightening the screw in the intermediate component, or neck, to lock the trial head with the other hand. If a surgeon is using an eccentric head and it inadvertently rotates, the direction of eccentricity may change. If the direction of eccentricity is changed, the final prosthesis will not be an accurate anatomical restoration of the humeral head as desired. Also, the torque generated by the twisting action in securing the components of the prosthesis may result in the humerus in patients with weak bones to approach the point of potential fracture.

Attempts have been made to provide shoulder prostheses with adjustability of the articulating head with respect to the distal stem. One such product uses a trial head to determine the position of the final implant. This product adjusts the positions of the trial head by placing a hex driver into holes on the side of the head. The technique is not optimal in that it is very difficult to adjust from the side because of the lack of space in the surgical site. If the surgeon cannot adjust the head properly, he may not get an exact anatomical restoration of the humeral head, or he may not be able to tighten the screws to lock the proper position. It may be also difficult to make the adjustment without damaging the soft tissue around the proximal humerus. Finally, the technique may be incompatible with less invasive approaches where access to the surgical site is limited due to small incisions.

The present invention attempts to overcome at least some of the aforementioned problems.

SUMMARY OF THE INVENTION

During shoulder surgery, surgeons are required to adjust the trial humeral head in a desired position when utilizing a humeral shoulder prosthesis with an articulating neck. Doing so with the surgeon's hands is very difficult because of limited space to maneuver and due to the slippery conditions of the trial head. The trial head handle of the present invention solves these problems. It contains two bosses on the shaft which mate with the openings in the trial head. The surgeon is able to rotate and position the trial head until the best position is found. The handle also contains a wide handle portion with large flats to provide an optimal grip for the hand in the slippery environment of the shoulder surgery.

The handle and the shaft may be cannulated so that a driver may be placed through the handle instrument and through the trial head and into the trial neck or ball-cylinder that links the trial head and trial stem. Tightening a screw in this ball-cylinder locks the trial head in its proper position. The surgeon may also prevent an unwanted movement of the ball-cylinder and the trial head while locking the intermediate components by resisting this movement with the handle. This resistance also prevents torque of the stem on the humerus. Such torque may otherwise cause a proximal humerus fracture. The accurate position of the prosthesis possible with the instrument of the present invention results in a prosthesis that mimics during trialing the anatomical orientation of the natural humeral head.

The global AP is a shoulder replacement system that allows adjustability in all directions of the humeral head relative to the humeral stem. The shoulder replacement stem utilized with the instrumentation of the present invention has been designed into the system so that the end result of the shoulder replacement is a humeral head resting squarely on the resected humerus bone. Such stable placement on the resected bone may occur even if the patient has atypical anatomy or the surgeon's resection of the humeral head is not optimum.

An instrument is advantageous to easily manipulate the position of the humeral head during trialing without damaging the humerus or surrounding soft tissue. The trial head handle assists in this surgery. The trial head handle includes a handle and a shaft. Two bosses are positioned at the end of shaft which mate with openings in the trial head. When both bosses are mated with the trial head openings, the handle can be turned or rotated until the trial head has been correctly positioned.

Due to varying anatomy and imperfect surgical resection of the humeral head, the instrument to be used with the articulating humeral stem component has been designed so that the humeral head may be positioned, for example, 15° or more in any direction from which would be considered typical for a humeral head position. The surgical technique to be utilized with the present invention requires that the surgeon determine the final orientation of the implant by first obtaining proper orientation of trial components. To obtain this proper orientation of trial components, the trial head is placed over an intermediate component such as a ball-cylinder between the trial stem or broach and the humeral head.

The ball-cylinder may be placed into the hole in the trial stem or broach. The ball portion of the ball-cylinder allows for rotation in any direction of, for example, 15° or more. The trial head handle may then be mated with the trial head. The trial head handle is used to control and position the trial head until the trial head seats uniformly against the resected surface and has the appropriate coverage at the articular margin.

When the optimum trial head position is found, a driver may be placed through both the trial head handle and the trial head and into the ball-cylinder. A screw may be tightened in the ball-cylinder to lock the position of the trial head relative to the brooch.

The trial head handle may assist the surgeon in obtaining an optimum surgical result, because the surgeon has much better control of the positioning of the trial head. Utilizing a handle to position the trial, holding it while locking the ball-cylinder into place becomes less of an issue because the trial, which may be slippery, does not need to be handled and the surgeon's hands no longer obstruct the view of the entire surgical site.

The trial head handle also prevents any rotation of the trial head while tightening the ball-cylinder screw. Rotation of a trial eccentric head may result in the lack of coverage of the final humeral head on the articular margin. Such rotation may result in an imperfect anatomical reconstruction causing complications to the patient. Also, if the stem rotates, the humerus may be stressed causing additional potential issues.

According to one embodiment of the present invention, there is provided a kit for use in performing a trial reduction in joint arthroplasty. The kit includes a trial stem assembly including a first component, a second component selectably moveable with respect to the first component, and a fastener for securing the first component to the second component. The kit also includes an articulating trial component removeably fixedly secured to the trial stem assembly and a driver for cooperation with the fastener to secure the first component to the second component. The kit also includes a handle. The handle has a first feature for permitting the driver to pass through the handle and a second feature for orientably connecting the handle to the articulating trial component.

According to another embodiment of the present invention there is provided a tool assembly for use in performing a trial reduction in joint arthroplasty using a trial stem assembly having a first component and second component connected by a fastener and having an articulation trial component. The tool assembly includes a driver for cooperation with the fastener to secure the first component to the second component and a handle. The handle has a first feature for permitting the driver to pass through the handle and a second feature for orientably connecting the handle to the articulating trial component According to still another embodiment of the present invention there is provided a tool for use with a driver for use in performing a trial reduction in joint arthroplasty using a trial stem assembly having a first component and second component connected by a fastener secured by the driver and having an articulation trial component. The tool assembly includes a handle. The handle has a first feature for permitting the driver to pass through the handle and a second feature for orientably connecting the handle to the articulating trial component.

According to still another embodiment of the present invention there is provided a trial for use in performing a trial reduction in joint arthroplasty. The kit includes a trial stem assembly including distal stem component, a proximal neck component selectably moveable with respect to the distal stem component, and a fastener for securing the proximal neck component to the distal stem component. The proximal neck component includes a resilient portion thereof cooperative with a distal end of the fastener and a longitudinal opening. The opening includes internal threads formed thereon. The distal stem component defines a seat therein for receiving the resilient portion of the proximal neck component. The fastener includes external threads formed on a proximal portion thereof. The external threads of the fastener threadably engage with internal threads formed on the proximal neck component. The kit also includes an articulating trial component removeably fixedly secured to the proximal neck component of the trial stem assembly. The fastener urges the resilient portion of the proximal neck component into engagement with seat of the distal stem component.

According to still another embodiment of the present invention there is provided a trial for use in performing a trial reduction in joint arthroplasty. The trial includes a trial stem assembly including a distal stem component, a proximal neck component selectably moveable with respect to the distal stem component, and a fastener for securing the proximal neck component to the distal stem component. The proximal neck component includes a resilient portion thereof cooperative with a distal end of the fastener and a longitudinal opening. The distal stem component defines a seat therein for receiving the resilient portion of the proximal neck component. The trial also includes an articulating trial component removeably fixedly secured to the proximal neck component of the trial stem assembly. The articulating trial component has an articulating surface and an opposed surface, opposed to the articulating surface. The articulating trial component defines an aperture extending from the articulating surface to the opposed surface. A tool may be inserted through the aperture to engage the fastener to secure the proximal neck component to the distal stem component.

The technical advantages of the present invention include the ability to accurately position the humeral trial head. For example, according to one aspect of the present invention, a tool assembly is provided for use in performing a trial reduction in humeral joint arthroplasty using a humeral stem assembly having a first component and a second component connected by a fastener and having an articulating humeral head component. The tool assembly includes a driver for cooperation with the fastener to secure the first component to the second component, and a handle. The handle has a first feature permitting the driver to pass through the handle and a second feature for orientably connecting the handle to the articulating trial component. Thus, the present invention provides for the ability to accurately position the trial humeral head utilizing the handle.

The technical advantages of the present invention further include the ability to allow for a less invasive procedure than would be possible if one needed to position the trial head with the hand. For example, according to another aspect of the present invention, a tool assembly is provided for use in a trial reduction in a shoulder joint arthroplasty. The tool assembly includes a driver for cooperation with the fastener to secure the first component to the second component of a humeral trial stem assembly. A handle is also provided with the tool assembly and includes a first feature for permitting the driver to pass through the handle and a second feature orientably connecting the handle to the articulating humeral head. Thus, the present invention provides for an ability to provide for a less invasive procedure than would be possible if positioning the trial head with the hand.

The technical advantages of the present invention further include the ability to manipulate the head of a humeral stem assembly without having to visually see the head. With the limited space in the surgical site, the surgeon can easily manipulate the position of the trial head. For example, according to another aspect of the present invention, a tool assembly is provided including a driver for cooperation with the fastener to secure the distal trial stem with the proximal neck. The assembly also includes a handle having a first feature in the form of a cylindrical opening to permit the driver to pass through the handle and a second feature in the form of a protrusion which cooperates with a feature on the articulating humeral head to orientably connect the handle to the articulating humeral head. Thus, the present invention provides for the ability to manipulate the humeral head without having to see the head. Such a device permits for a less invasive procedure as the incision may be smaller in that the vision of the head is not required.

The technical advantages of the present invention further include the ability to not need to hold a slippery humeral head. For example, according to yet another aspect of the present invention, a tool assembly for use in humeral joint arthroplasty is provided. The tool assembly includes a driver for cooperation with the fastener to secure the distal humeral stem to the articulating neck component. The tool assembly further includes a handle having a first feature in the form of a longitudinal opening to permit the driver to pass through the handle and a second feature for connecting the handle to the articulating trial component. Thus, the present invention provides the ability to utilize a handle with a feature to hold a feature on the articulating humeral head so that the articulating humeral head does not need to be held manually by the surgeon.

The technical advantages of the present invention further include the ability to prevent inadvertent rotation of the humeral head. The unwanted rotation of the trial head while locking the intermediate component, or ball-cylinder or trial neck, may interfere with the proper final placement of the implant. For example, according to yet another embodiment of the present invention, a tool assembly for use in performing shoulder joint arthroplasty is provided. The tool assembly is utilized for securing a distal stem component to a proximal neck component which are connected to each other by a fastener. The tool assembly includes a driver for cooperation with the fastener and a handle that includes a feature which permits the driver to pass through the handle and a feature on the handle for connecting the handle to the humeral head. Thus, the surgeon may utilize the handle to adjust the articulating neck with respect to the distal stem to avoid rotation of an eccentric head to properly position the head against the resected surface of the humerus.

The technical advantages of the present invention further include the ability to avoid unwanted rotation of the stem. The rotation of the stem may cause stress to the humerus which may otherwise lead to a possible fracture. For example, according to yet another aspect of the present invention, a tool assembly for use in shoulder joint arthroplasty is provided to secure an articulating neck component to a distal stem component utilizing a screw. A driver is used to rotate the screw and a handle is provided with an opening for the passage of the driver through the handle. The handle includes a feature for cooperation with an articulating head feature such that the head may be held in a fixed position while the screw is tightened by the driver, thereby avoiding a torque being transmitted through the stem of the prosthesis and into the humerus. Thus, the present invention provides for prevention of unwanted rotation of the stem and related unnecessary stress to the humerus.

The technical advantages of the present invention further include the ability to avoid damage caused to the surrounding soft tissue. For example, according to another aspect of the present invention, a tool assembly is provided including a driver for cooperation with the fastener to secure the distal trial stem with the proximal neck. The assembly also includes a handle having a first feature in the form of a cylindrical opening to permit the driver to pass through the handle and a second feature in the form of a protrusion which cooperates with a feature on the articulating humeral head to orientably connect the handle to the articulating humeral head. Thus, the present invention provides for the ability to avoid damage to the surrounding soft tissue.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
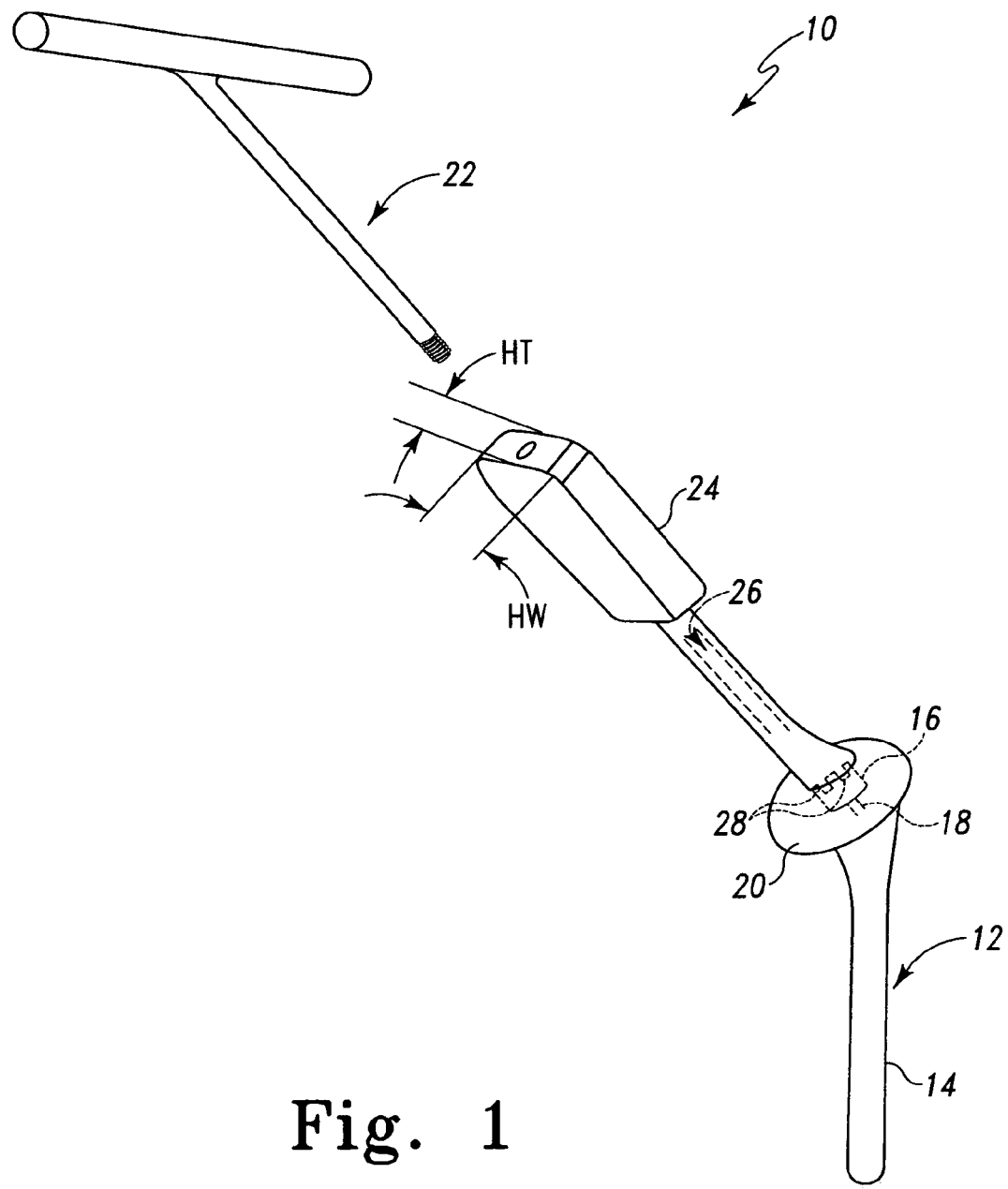
FIG. 1 is a perspective view of a kit for use in performing a trial reduction in joint arthroplasty in accordance with an embodiment of the present invention.

According to the present invention and referring now to FIG. 1, a kit 10 for use in performing a trial reduction in joint arthroplasty is shown. The kit 10 includes a trial stem assembly 12 including a first component 14. The first component 14 may, as shown in FIG. 1, be in the form of a distal trial stem. The distal trial stem 14 may be a distal trial stem for a humerus as part of a shoulder prosthesis or may be a distal trial stem for a hip prosthesis in the form of a distal trial stem for a femur. It should be appreciated that the distal trial stem may be fitted into any long bone.

The trial stem assembly 12 further includes a second component 16 which is selectively moveable with respect to the first component 14. The second component 16 may be in the form of a proximal neck component and may, for example, be a proximal humeral neck component of a shoulder prosthesis. The second component 16 may be in the form of an intermediary component or be in the form of a ball-cylinder component or trial neck. The trial stem assembly 12 may further include a fastener 18. The fastener 18 is used for securing the first component 14 to the second component 16. The trial stem assembly 12 may, as shown in FIG. 1, include the second component 16 which is moveable in respect to the first component 14 in any suitable fashion. For example, the second component 16 may articulate, or pivot, with respect to the first component 14.

The kit 10, as shown in FIG. 1, may further include an articulating trial component 20 which is moveably, fixedly secured to the trial stem assembly 12. The articulating trial component 20, as shown in FIG. 1, is in the form of a head component and may be, for example, a humeral head of a shoulder prosthesis. The articulating trial component 20 is removeably fixed to the trial stem assembly 12 in any suitable fashion.

The kit 10 further includes a driver 22 for cooperation with the fastener 18 to secure the second component 16 to the first component 14.

The kit 10, as shown in FIG. 1, may further include a handle 24. The handle 24 includes a first feature 26 for permitting the driver 22 to pass through the handle 24. The feature 26, as shown in FIG. 1, may be in the form of a longitudinal central opening for passage of the driver 22 there through. The handle 24 further includes a second feature 28 for orientably connecting the handle 24 to the articulating component 20.

Figure 2:
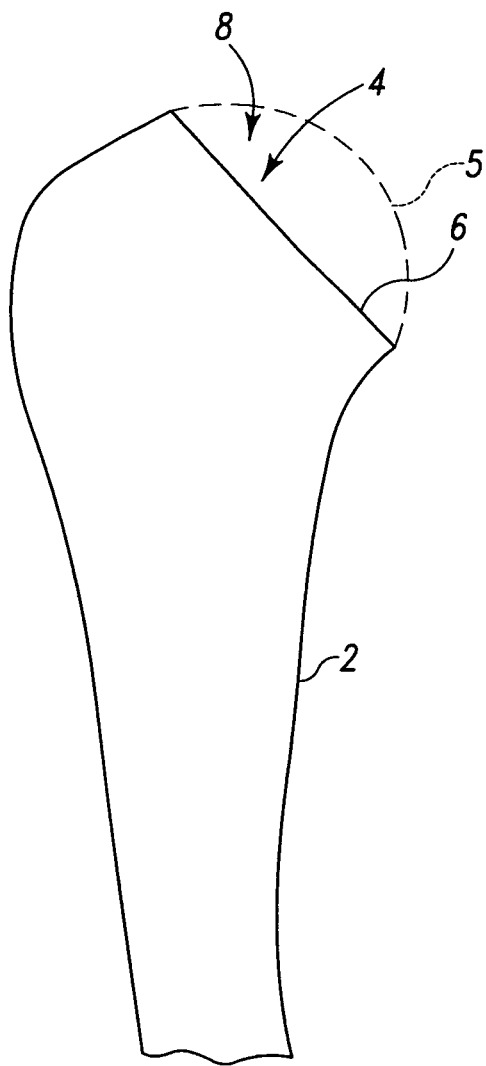
FIG. 2 is a plan view of a resected humerus that may utilize the kit of FIG. 1.

Referring now to FIG. 2, a long bone 2 is shown for use with the kit 10 of FIG. 1, according to the present invention. The long bone 2, of FIG. 2, may be any long bone of the human anatomy and may, for example, be a femur, or a tibia. As shown in FIG. 2, the long bone may be in the form of a humerus. The long bone 2 includes an intramedullary canal 4 extending longitudinally through the long bone 2. The long bone 2 may be resected and have head 5 of the long bone 2 resected along resected surface 6. The resection of the long bone 2 may expose the canal 4 such that a cavity 8 may be prepared in the canal 4 by the use of a drill, reamer, or a broach, or similar instrument.

Figure 3:
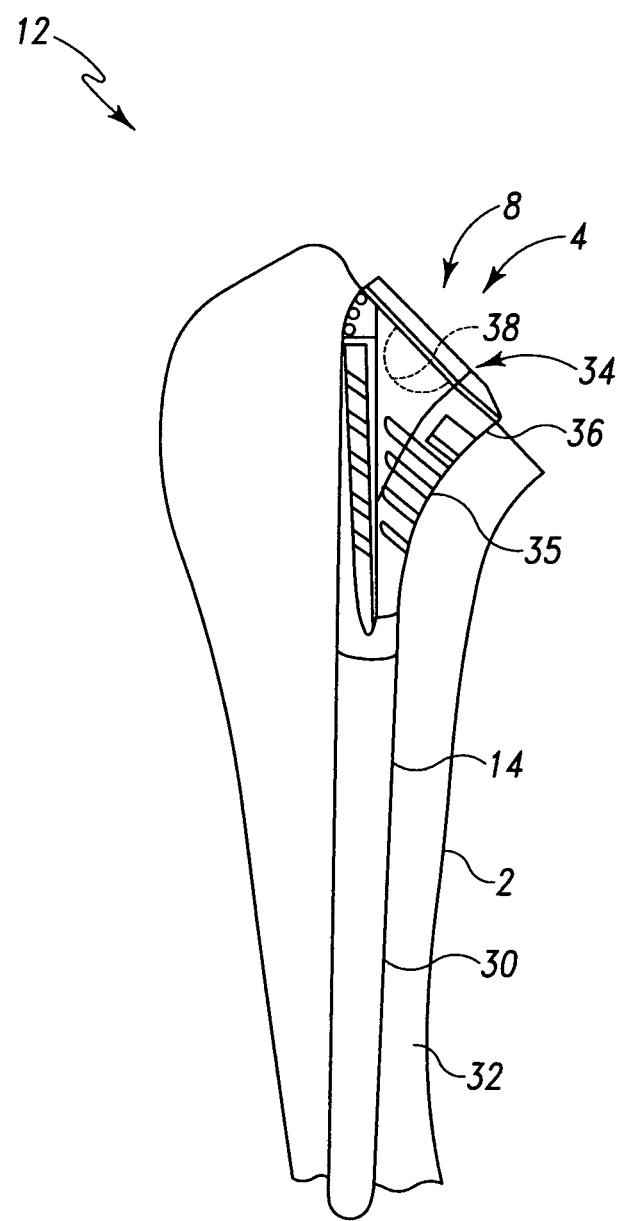
FIG. 3 is a perspective view of a prosthetic humeral stem trial of the humeral stem trial assembly of the kit of FIG. 1.

Referring now to FIGS. 3-7, the trial stem assembly 12, of the present invention, is shown in greater detail. Referring now to FIG. 3, the trial stem assembly 12 may include a humeral trial stem 14 which may be fitted into cavity 8 formed in canal 4 of the long bone 2. The humeral trial stem 14 may include a cylindrical distal stem 30 and a proximal body 36 extending proximally from the cylindrical distal stem 30. The distal stem 30 may alternately include longitudinal spaced apart flutes (not shown) to assist in the securing of the humeral trial stem 14 in the canal 4 of the long bone 2. The humeral trial stem 14 may further include a cavity 34 formed in the proximal body 36 of the humeral trial stem 14. The cavity 34 may define a concave surface, or pocket, 38 for receiving the ball-cylinder 16 of the trial stem assembly 12.

The proximal body 36 may include broach teeth 35 for broaching the canal 4 of the long bone 2. The broach teeth 35 may serve to eliminate the need for a separate broaching step in the arthroplasty procedure. It should be appreciated that a separate broach may be utilized with the invention of the present invention. Also it should be appreciated that the humeral trial stem 14 may also be provided without the broach teeth.

Figure 4:
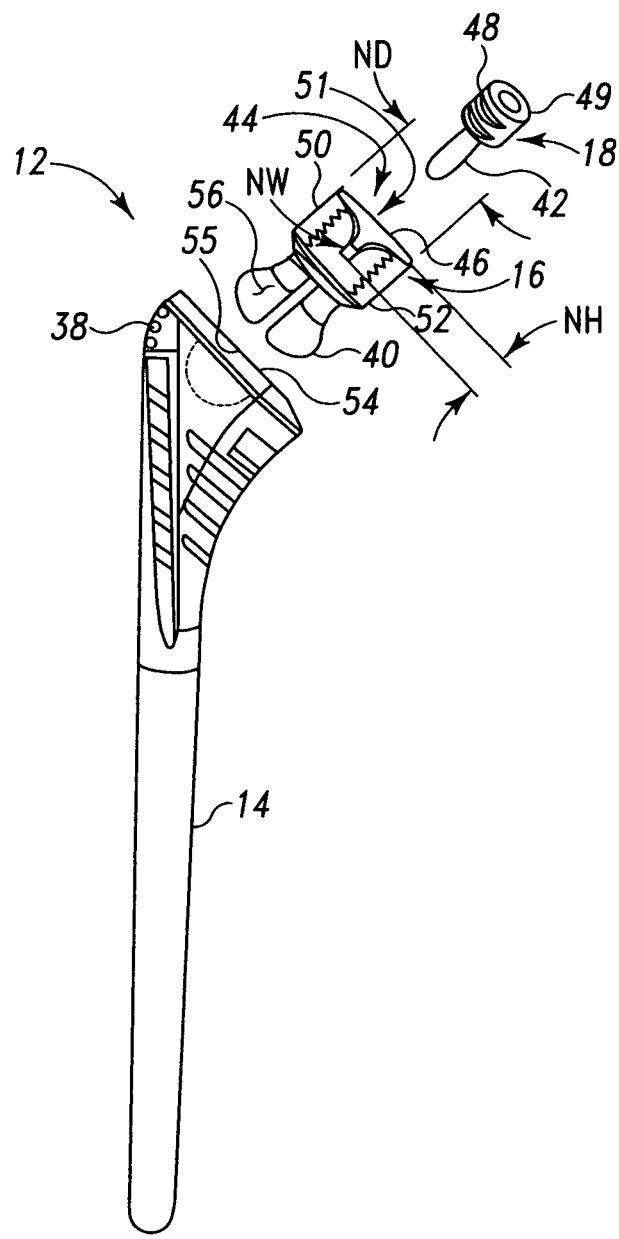
FIG. 4 is an exploded perspective view of the humeral trial stem assembly of the kit of FIG. 1 using the prosthetic humeral trial stem of FIG. 3.

Referring now to FIG. 4, the trial stem assembly 12 is shown in an exploded view with the distal stem component 12, the proximal neck component 16, and the fastener 18 shown as separate components in their position to be assembled to form the trial stem assembly 12.

The proximal neck component 16, may, as is shown in FIG. 4, be in the form of an intermediate component, or a ball-cylinder component, and may be a part of, for example, the humeral trial stem assembly 12 for use in shoulder orthopedic arthroplasty surgery. The proximal neck component 16 may include a feature to make the proximal neck component 16 moveable with respect to the stem 14. The fastener 18 may be utilized for securing the proximal neck component 16 to the stem 14. The proximal neck component, as shown in FIG. 4, may include a resilient portion 40 of the proximal neck component 16. The resilient portion 40 may be cooperative with a distal end 42 of the fastener 18.

The proximal neck component 16 may further include a longitudinal opening 44 extending longitudinally through the proximal neck component 16. The longitudinal opening 44 may define internal threads 46 formed on the proximal neck component extending outwardly from the longitudinal opening 44. The distal stem component 12 includes the seat, or concave surface, 38 for receiving the resilient portion 40 of the proximal neck component 16. The fastener 18 may include external threads 48 formed on a proximal portion 49 of the fastener 18. The external threads 48 of the fastener 18 may be threadably engageable with the internal threads 46 formed on the proximal neck component 16.

As shown in FIG. 4, the proximal neck component 16 includes the proximal cylindrical portion 50 including surface 52 which may be generally cylindrical and defined by diameter ND. Alternatively, the portion 50 may be frustum-conical or have a taper defined by, for example, an included angle. The humeral neck component 16 may further include the resilient portion 40 which may include a plurality of spaced apart fingers having longitudinal slots 54 positioned between the fingers of the resilient portion 40. The resilient portion 40 may include a convex external surface 56 which may be generally spherical or approximate a sphere for cooperation with the concave surface 55 of the seat 38.

As shown in FIG. 4, the cylindrical portion 50 of the proximal neck component 16 includes an orientation feature or key in the form of notch 51. The notch 51 cooperates with a feature on the trial head to provide angular orientation of the trial head with respect to the proximal neck component 16. The notch 51 may be a rectangular notch through a wall of the cylindrical portion 50 and extending a distance NH from the proximal end of the cylindrical portion 50. The notch 51 may have a width NW. It should be appreciated that the feature or notch 51 may have an oval, cylindrical or other shape. Alternatively the feature 51 may be a positive feature in the form of a protrusion or other shape. In such case the humeral head would have a void to match the positive feature.

Figure 5:
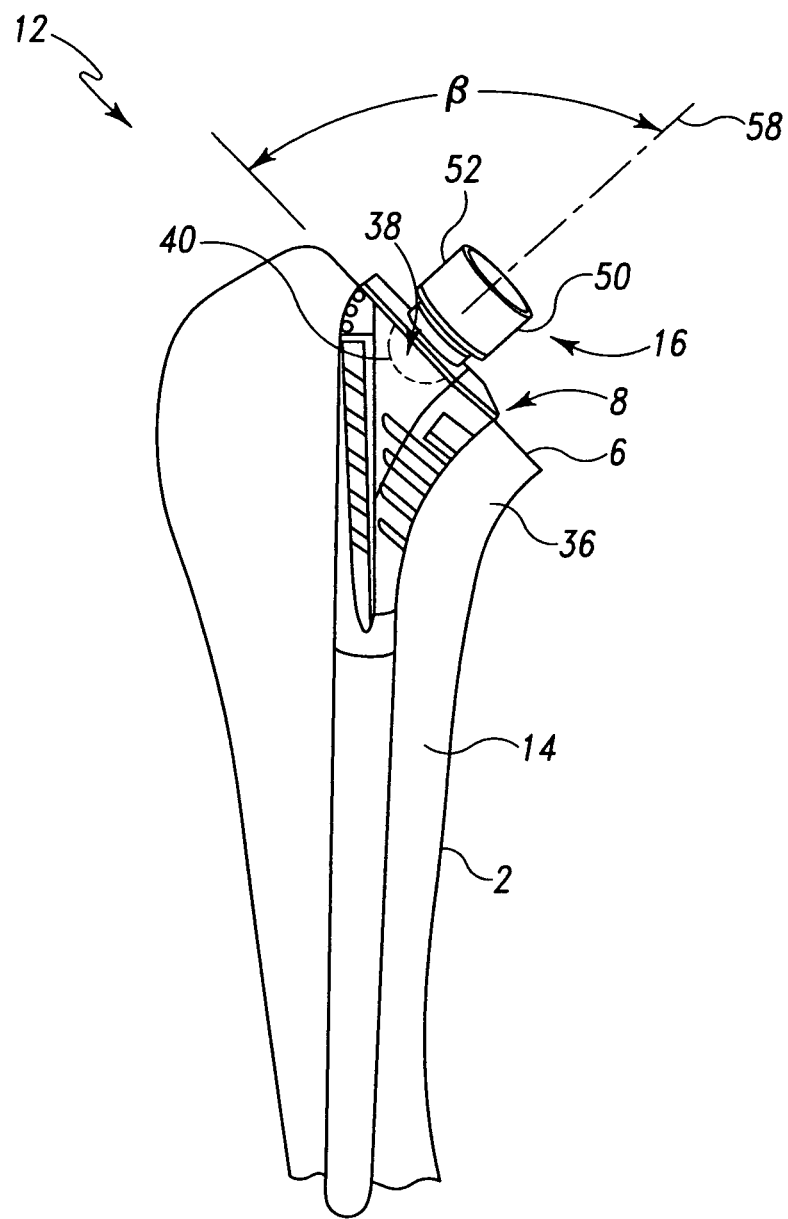
FIG. 5 is a perspective view of the humeral stem assembly of FIG. 4.

Referring now to FIG. 5, the trial stem assembly 12 is shown in an assembled condition. The distal stem component 14 is shown in position in cavity 8 of the long bone 2. The proximal neck component 16 is assembled to stem 14 with the centerline 58 of the neck component 16 at an angle β with respect to resected surface 6 of the long bone 2. The center line 58 of the proximal neck component 16 is preferably normal, or perpendicular, to the resected surface 6 such that the articulating trial component 20 may properly seat against, or be positioned with respect to the resected surface 6 of the long bone 2.

Figure 5A:
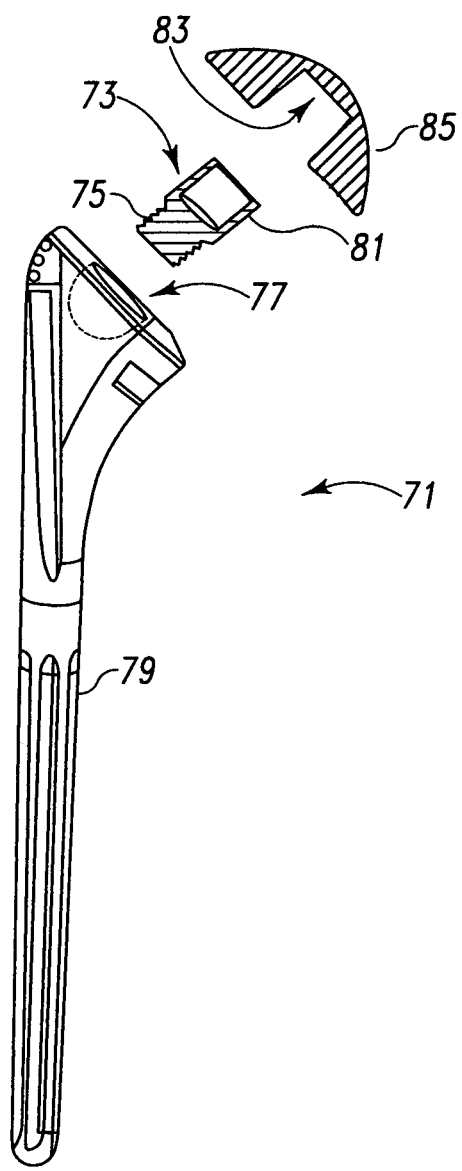
FIG. 5A is a an exploded perspective view of a prosthetic humeral implant assembly, including a humeral head, neck, and stem, that may be utilized as a permanent implant after the use of the humeral stem trial assembly of the kit of FIG. 1 to perform a trial reduction.

For example, and referring now to FIG. 5A, a humeral implant assembly 71 is shown. The humeral implant assembly 71 is utilized in shoulder joint arthroplasty in conjunction with the kit 10 of FIG. 1 including the humeral trial stem assembly 12. The humeral implant assembly 71 is utilized after the trial reduction is performed. If the trial reduction is successful. The size and orientation of the trial assembly 12 is replicated, for example, in the surgery room and the humeral implant assembly 71 is oriented to the same angles and orientation as the successful trial assembly. The humeral implant assembly 71 includes a solid neck stem or connector 73. The connector 73 includes a spherical end 75 that fits into a tapered cavity 77 of humeral implant distal stem 79 at the selected angle. The connector 73 includes a male taper 81 that mates with a female taper 83 on implant humeral head 85.

It should be appreciated that alternatively the humeral articulating component for use in this invention may be concave rather than convex. In such configurations the glenoid component is convex rather than concave. Such a product is sold by DePuy Orthopaedics, Inc., Warsaw, Ind., as the Delta® Shoulder.

Figure 7:
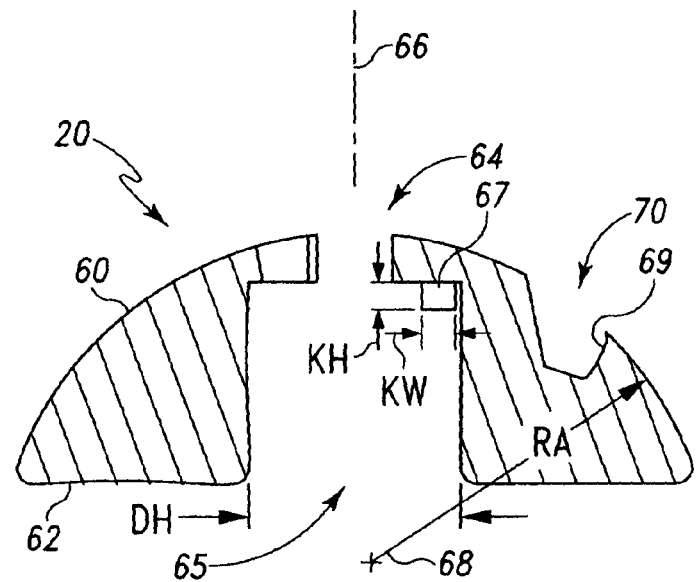
FIG. 7 is a cross section view of FIG. 6 along the line 7-7 in the direction of the arrows.
Figure 6:
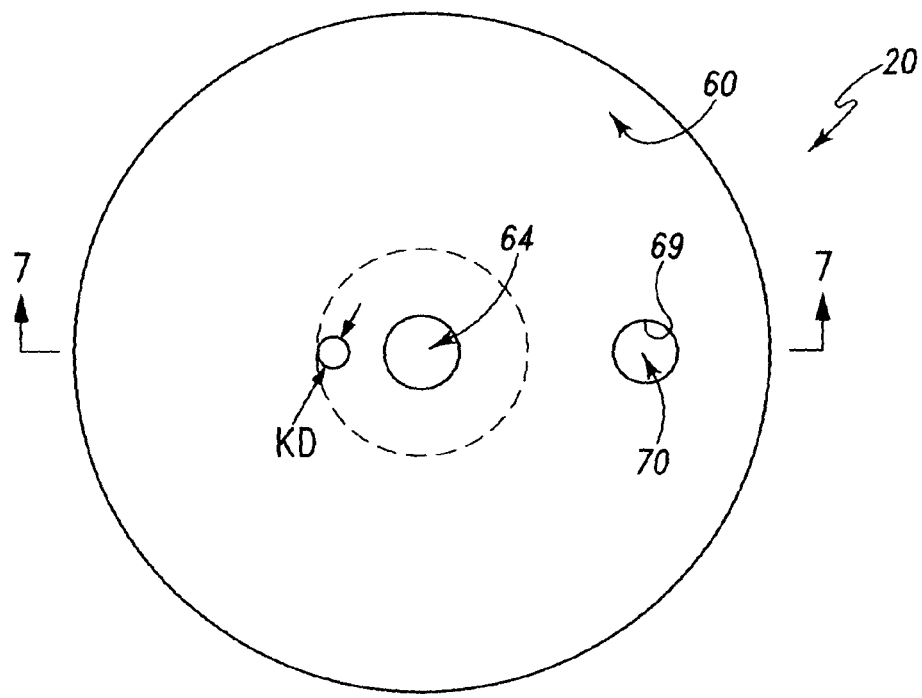
FIG. 6 is a top view of a humeral trial head that may be used with the trial stem assembly of the kit of FIG. 1.
Figure 14:
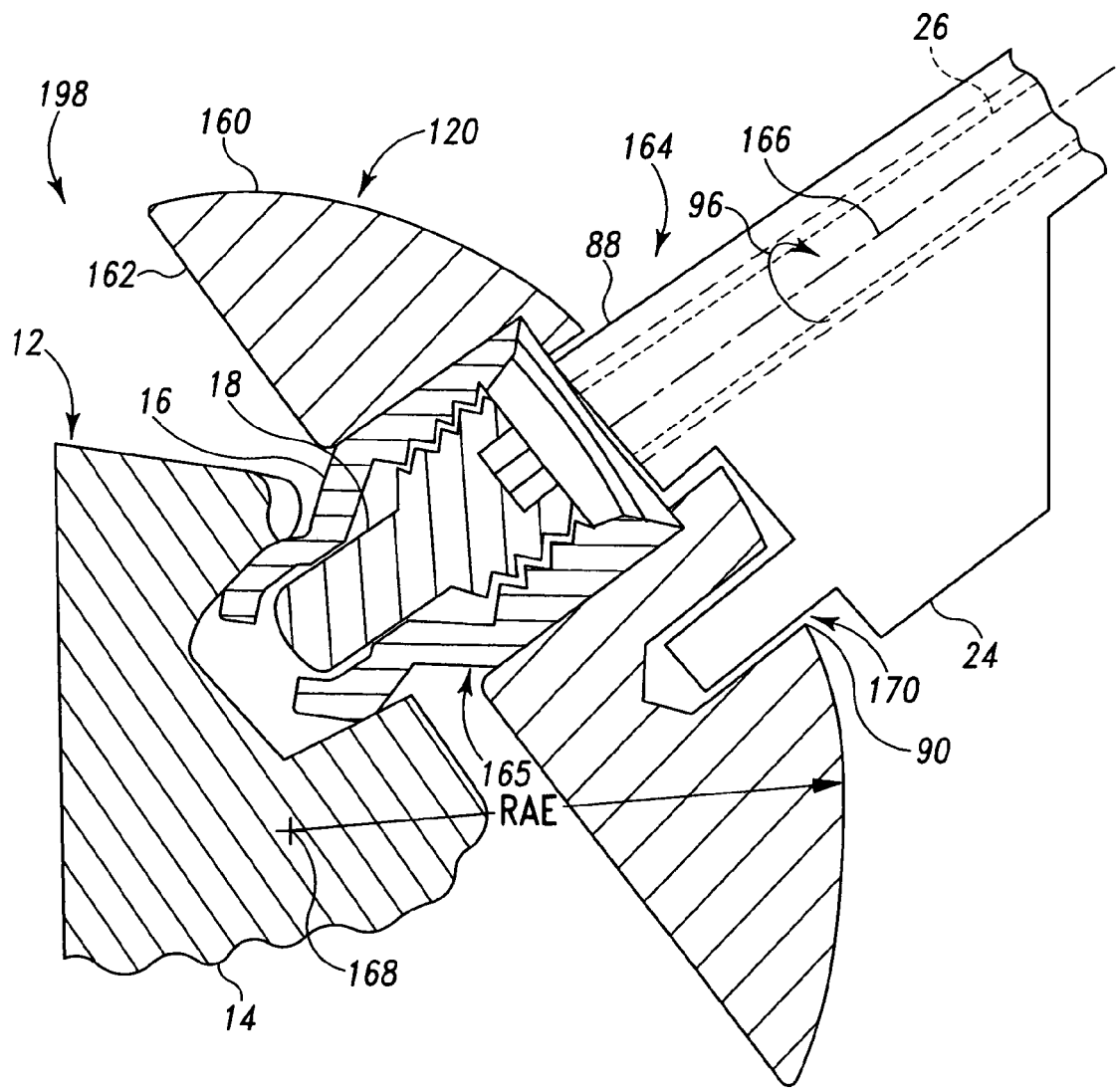
FIG. 14 is a partial plan view partially in cross section view of another embodiment of the present invention in the form of a kit with an eccentric humeral head showing the connection of the handle to the head and screw in detail.

Referring now to FIGS. 6 and 7, the articulating trial component 20 is shown in greater detail. The articulating trial component 20, as shown in FIG. 7, may be a symmetrical component. It should be appreciated that the articulating trial component 20 may also be eccentric. Such an eccentric trial component is shown in FIG. 14 herein. The articulating trial component 20, as shown in FIGS. 6 and 7, is in the form of humeral trial head. The articulating trial component 20 is adapted to be removeably fixedly secured to the proximal neck component 16 of the trial stem assembly 12, of FIG. 1. The articulating trial component 20 includes an articulating surface 60 and an opposed surface 62. The opposed surface 62 is opposed to the articulating surface 60.

The articulating trial component 20 defines a longitudinal opening 64 extending from the articulating surface 60 to the opposed surface 62. It should be appreciated that the tool in the form of the driver 22, of the kit 10, may be easily passed through the longitudinal opening 64 of the articulation trial component 20.

As shown in FIGS. 6 and 7, the articulating trial component 20 may be defined by, for example, longitudinal center line 66. An origin 68 extending through the longitudinal center line 66 may define in cooperation with radius A extending from origin 68 to the articulation surface 60 to define the articulation surface 60 of the articulating trial component 20.

The longitudinal opening 64 may, as shown in FIG. 6, be centrally located with respect to the longitudinal axis 66 of the articulating trial component 20. The articulating trial component 20 may, as shown in FIG. 6, include a second cavity 68 defined by internal wall 69 formed in the articulating surface 60 of the articulating trial component 20.

The articulating trial component 20 may further include an internal connection 65 in the form of, for example an opening, centrally located along the longitudinal center line 66 of the articulating trial component 20. The internal connection 65 of the articulating trial component 20 may be cylindrical and may be defined by, for example, diameter DH to mate diameter ND of proximal neck component 16. The fit between the articulating trial component 20 and the proximal neck component 16 should be sufficient for successful trialing, but loose enough to assure easy disassembly after trialing.

Alternatively, the internal connection of the articulating trial component may be tapered and be defined by an included angle which is preferably similar to the included angle of the surface of tapered proximal neck component, such that the surface of the neck component may form a rigid connection with the internal tapered connection of the articulating trial component.

The articulating trial component 20 may further include an articulating trial component keying feature 67 in the form of a rectangular protrusion having a width KW, a depth KD and a height KH. The feature 67 may alternatively be cylindrical or any other simple shape. The articulating trial component keying feature 67 may extend from near periphery of the cylindrical opening 65 in the articulating trial component 20. The keying feature 67 may be in alignment with the opening 70. The articulating trial component keying feature 67 mates with the notch 51 formed in proximal neck component 16. The keying feature 67 and the notch 51 serve to provide angular orientation of the articulating trial component 20 with the proximal neck component 16. This orientation is prevents angular movement of the articulating trial component 20 with respect to the proximal neck component 16 during trialing and may be helpful with replicating this orientation onto the implant assembly 71 of FIG. 5A, prior to implanting the implant assembly 71.

Figure 8:
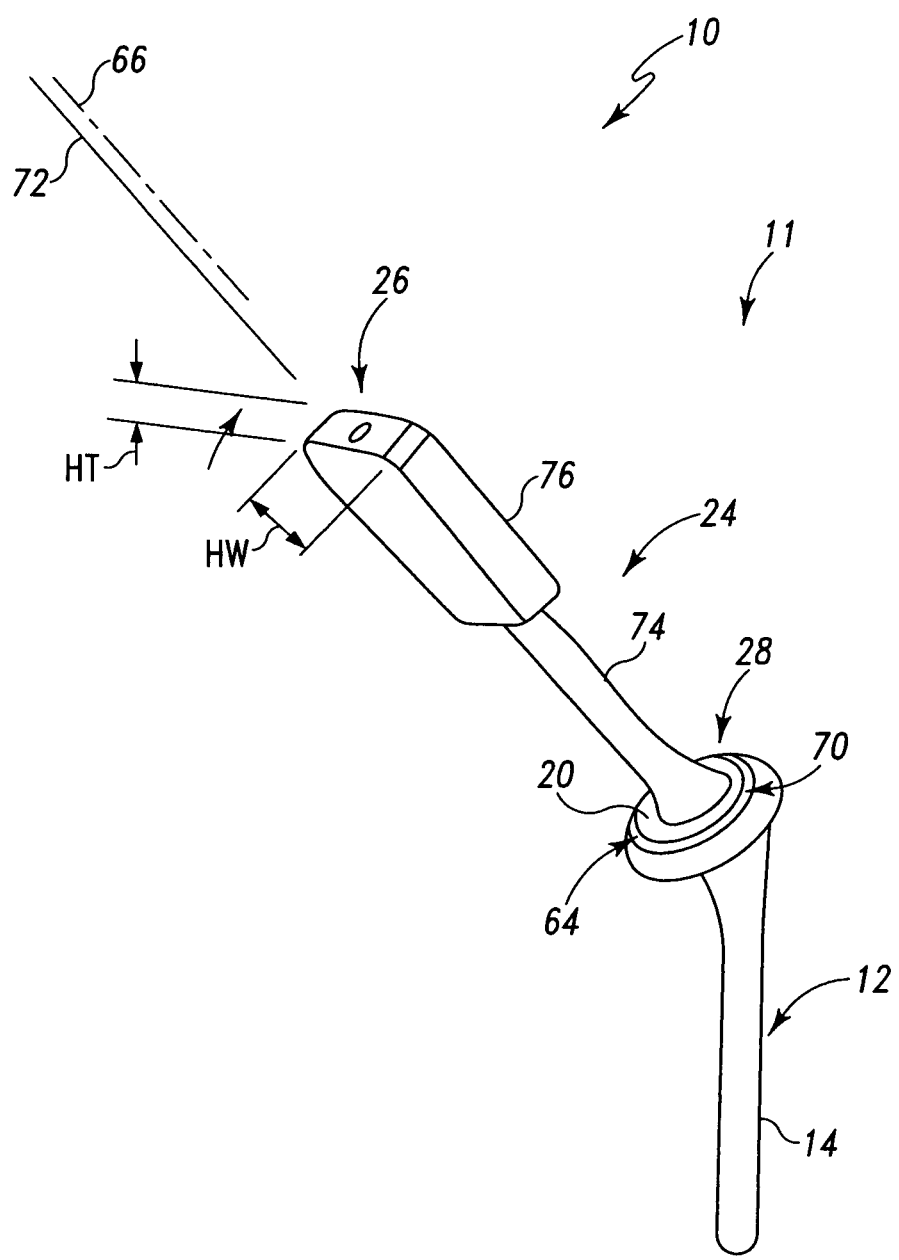
FIG. 8 is a perspective view of kit according to the present invention including a handle of the present invention in position on a humeral trial assembly of the present invention.
Figure 9:
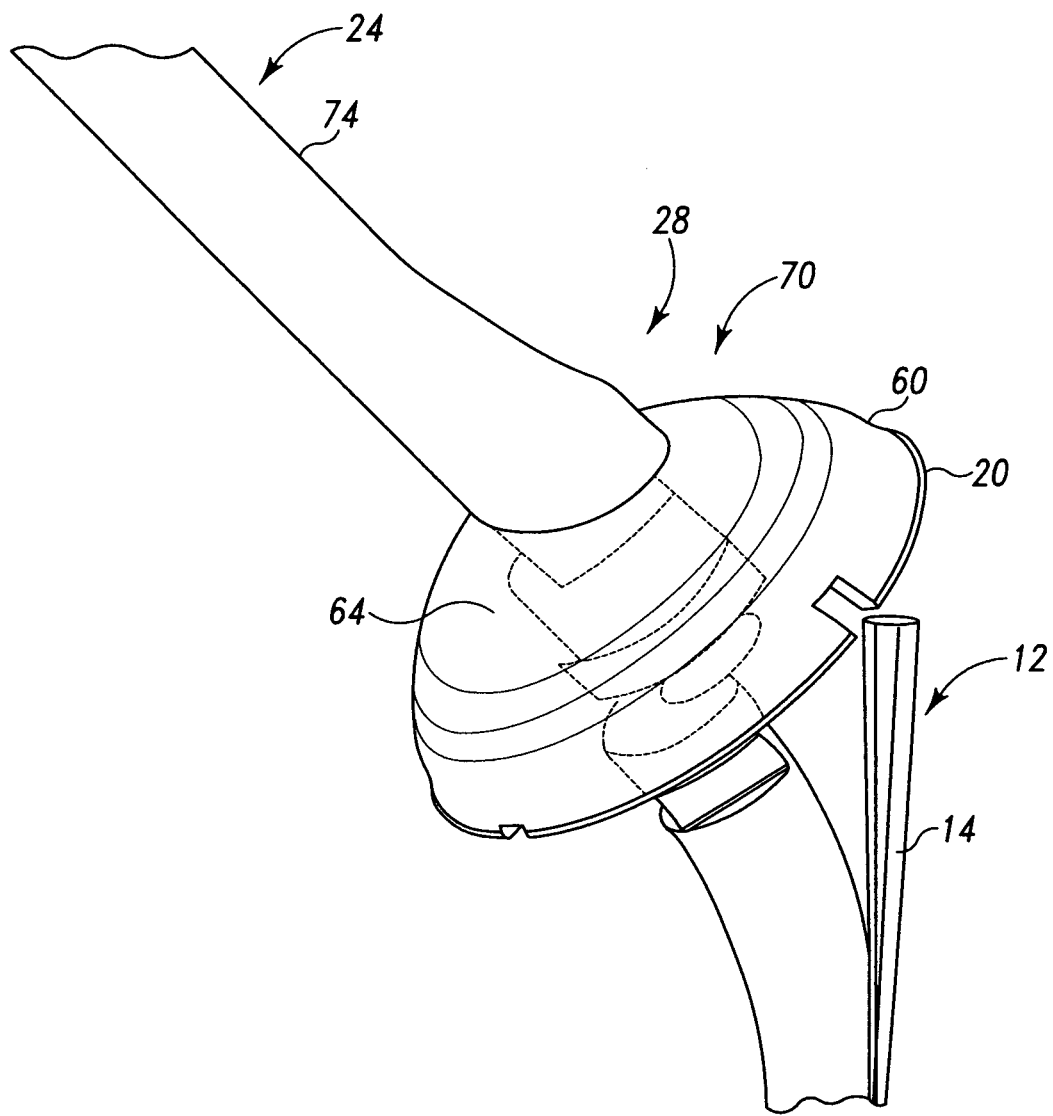
FIG. 9 is a partial perspective view of kit of FIG. 8 showing the head and connection of the handle in greater detail.

Referring now to FIGS. 8 and 9, the handle 24 of the kit 10, of FIG. 1, is shown in position on humeral prosthesis 11. The humeral prosthesis 11 includes the trial stem assembly 12 together with the articulating trial component 20.

The handle 24 is advanced in the direction of the center line 66 of the articulating trial component 20 and rotated such that the central internal opening 64 and the cavity 70 of the articulating trial component 20 align with second feature 28 formed on the shaft 74, of the handle 24. The handle 24, as shown in FIG. 8, preferably includes a gripping portion 76 that has a shape designed to resist torque. For example, the gripping portion 76 may have a shape other than a cylinder shape such that torque may be more easily resisted. For example and as shown in FIG. 8, the gripping portion 76 may have a rectangular cross-section defined by a thickness HT and a width HW.

Referring now to FIG. 9, the second feature 28 formed on the shaft 74 of the handle 24 is shown engaged with the central cavity 64 and the second cavity 70 formed into articulating surface 60 of the articulating trial component 20.

Figure 10:
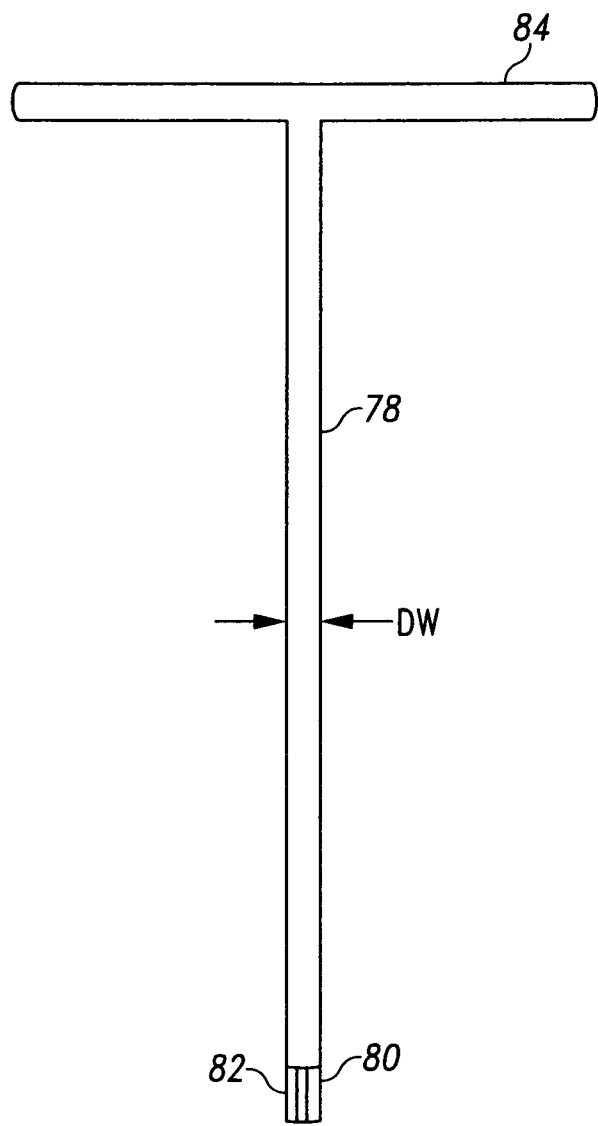
FIG. 10 is a plan view of driver a use with the kit of FIG. 8.

Referring now to FIG. 10, the driver 22 of the kit 10 is shown in greater detail. The driver 22 may have any suitable shape but, preferably, includes a shaft portion 78 which may, for simplicity, be circular or may be hexagonal. The shaft portion 78 of the driver 22 may be defined by a diameter DW which is smaller than the longitudinal opening 64 of the articulating trial component 20, as well as the longitudinal opening 26 of the handle 24, such that the connector 80 in the form of a bit or tip of the driver 22 may engage with the fastener 82 formed on fastener 18. The connector 80 may have an external hexagonal shape that may mate with an internal hexagonal socket 82 formed in the fastener 18. The driver 22 may further include a T-shaped handle 84 for providing torque for the connector 80 of the driver 22.

Figure 11:
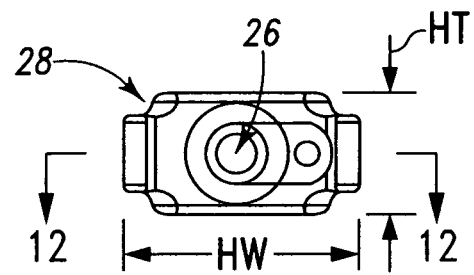
FIG. 11 is a top view a handle according to the present invention.
Figure 12:
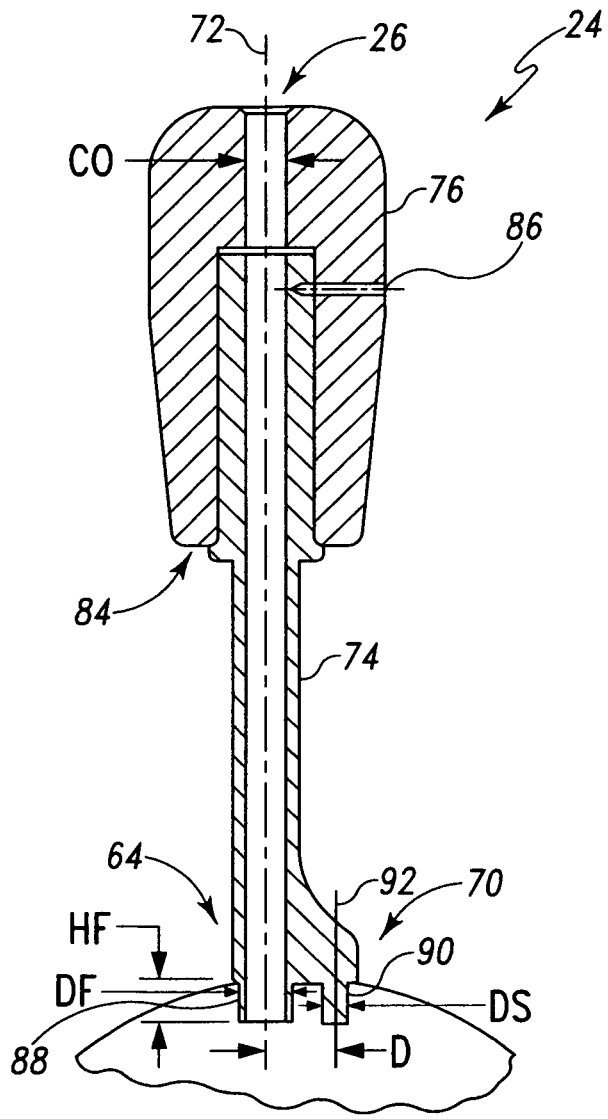
FIG. 12 is a cross section view of FIG. 11 along the line 12-12 in the direction of the arrows.

Referring now to FIGS. 11 and 12, the handle 24 of the present invention is shown in greater detail. While the handle 24 may have a unitary construction, as shown in FIG. 12, the handle 24 may have a two part construction, including the shaft 74 and gripping portion 76 which includes a longitudinal counter bore 84 that matingly fits with the shaft 74. A cross pin 86 may be utilized to secure the shaft 74 to the gripping portion 76. The shaft 74 may be made of any suitable, durable material and may, for example, be made of a metal. The gripping portion 76 may be made of a metal or a plastic and may as earlier described have a handle width HW which is greater than the handle thickness HT.

As shown in FIGS. 11 and 12, the handle 24 includes the second feature 28 for cooperation with the articulating trial component 20. The second feature 28 may, as shown in FIG. 12, be in the form of a first member 88 which extends outwardly from the shaft 74 and is positioned concentric with longitudinal center line 74 of the handle 24. The first member 88 may be defined by a diameter DF and a height HF. The first member 88 may be cylindrical and hollow. Longitudinal opening 26 may pass centrally through the first member 88.

The second feature 28 may, as shown in FIGS. 11 and 12, further include a second member 90 spaced from and parallel to the first member 88. The second member 90 may be cylindrical and may be defined by diameter DS and have a height HS which is the same as the height HF of the first member 88. The second member 90 defines a second member center line 92 which is parallel with first member center line 72 and spaced a distance O from the first center line 72.

The second member 90 may be a separate, discrete member from the first member 88, or may, as is shown in FIG. 12, the first member 88 and the second member 90 may be integral with each other. As is shown in FIG. 12, the first member 88 and the second member 90 may be integral with shaft 74.

Figure 13:
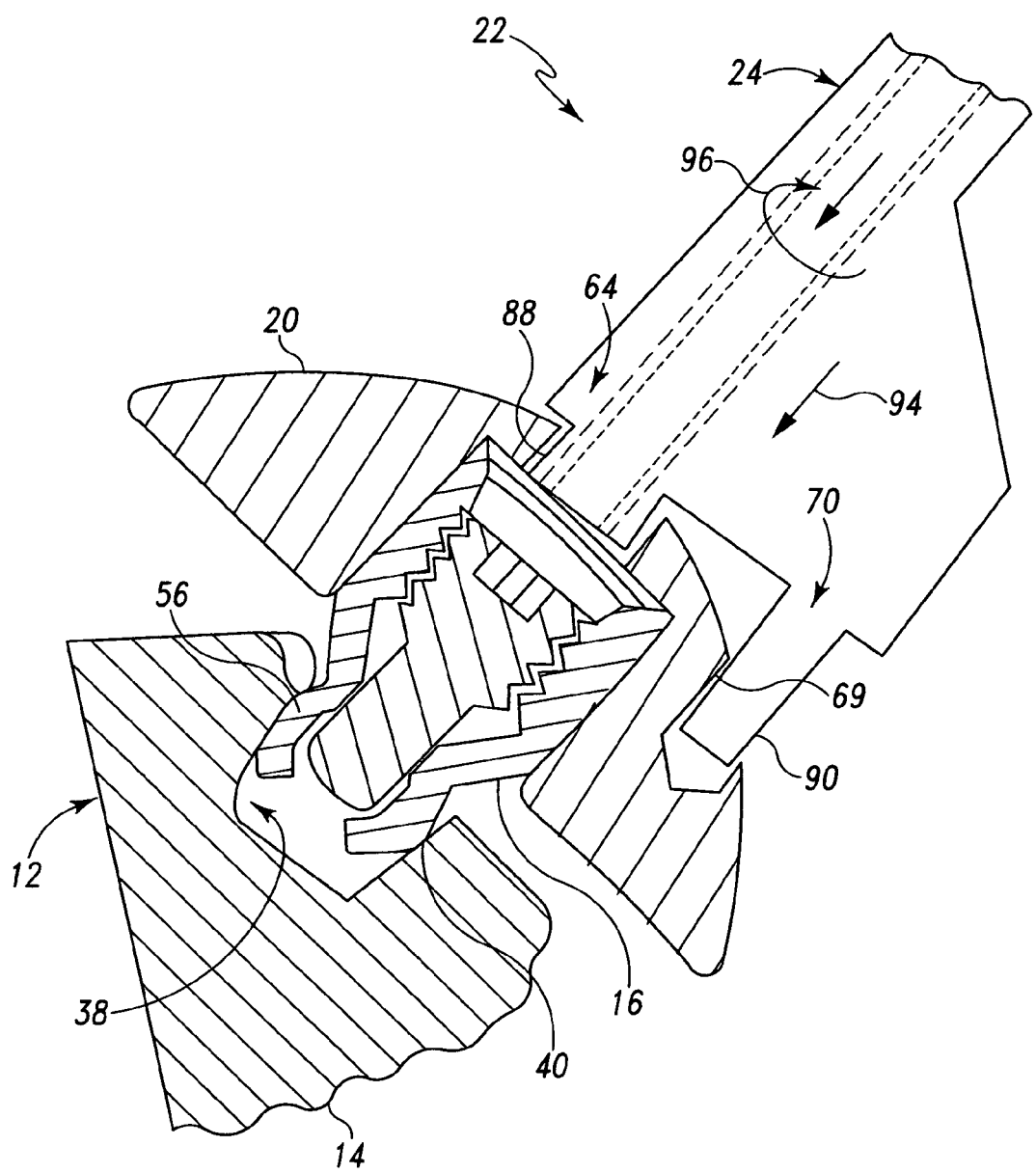
FIG. 13 is a partial plan view partially in cross section view of the kit of FIG. 1; showing the connection of the handle to the head and screw in greater detail.

Referring now to FIG. 13, the handle 24 is shown in position in use with the driver 22 and the trial stem assembly 12 to secure the articulating trial component 20 to the trial stem assembly 12.

As shown in FIG. 13, the trial stem assembly 12 includes distal stem 14 which includes a seat 38 which mates with resilient portion 40 of the proximal neck component 16 to selectably lock the neck component 16 and the articulating trial component 20 to the distal stem 14. The handle 24 is advanced in the direction of arrow 94 until the first member 88 fits within first opening 64 of articulating trial component 20. Simultaneously, the second member 90 is fitted into second cavity 70 formed in the articulating trial component 20.

The driver 22 may be kept in position the longitudinal opening 26 of the handle 24, or stored separately until needed. Once the driver 22 is in position the handle 24, the driver 22 is advanced in the direction of arrow 94 until the tip or bit 80 of the driver 22 engages fitting or socket 82 formed in the fastener 18. The driver 22 is rotated in the direction of arrow 96 until the distal end 42 of the fastener 18 extends toward the convex portion or resilient portion 40 of the proximal neck component 16 and advances the resilient portion radially outwardly. The convex surface 56 then engages the seat 38 of the distal stem, thereby securing the proximal neck component 16 in a proper position.

It should be appreciated that the surgeon may hold the handle 24 in the proper position with one hand while the surgeon rotates the driver 22 in the direction of arrow 96 at the same time so that the articulating trial component 20 may be placed in the proper position and so that the handle 24 may resist any torque applied by the driver 22 to either the trial stem assembly 12 or the articulating trial component 20.

Referring now to FIG. 14, yet another embodiment of the present invention is shown as trial assembly 198. The trial assembly 198 may include, for example, the trial stem assembly 12, of FIGS. 3-5, as well as an articulating trial component 120 which is different than the articulating trial component 20, of FIG. 13, in that the articulating trial component 120 is eccentric.

As shown in FIG. 14, the trial stem assembly 12 includes the distal stem 14 into which the proximal neck component 16 may be pivotally positioned. The fastener 18 is utilized to secure the proximal neck component 16 to the distal stem 14. The eccentric articulating trial component 120 includes an internal connection 165 which is similar in size and shape to the internal connection 65 of the articulating trial component 20, of FIG. 6. Therefore, the eccentric articulating trial component 120 may matingly fit to the surface 52 of the proximal neck component 16.

The eccentric articulating trial component 120 includes the articulating surface 160 and an opposed surface 162. The opposed surface 162 may rest on resected surface 6 of the femur or humerus 2. The eccentric humeral head 160 is defined by a radius RAE extending from origin 168 and located along an off-set center line 163 which is parallel to and space from a distance OF from the center line 166 of the internal connection 165 of the eccentric articulating trial component 120. The eccentric articulating trial component 120 may include a keying feature (not shown) like the keying feature 67 of the articulating trial component 120 of FIGS. 6 and 7.

It should be appreciated that as the handle 24 is rotated in, for example, the direction of arrow 96, the eccentric articulating trial component 120 may have its center line 163 moved around the center line 166 of the internal connection 165 of the eccentric articulating trial component 120. Therefore, it should be appreciated that the handle 24 may be utilized to orient the eccentric articulating trial component 120 in one of various positions around the center line 166 of the internal connection 165 of the eccentric articulating trial component 120.

As shown in FIG. 14, the handle 24 includes the first member 88 that may fit into first longitudinal opening 164 of the eccentric articulating trial component 120 as well as the second member 90 which may be fitted into second cavity 170 formed in eccentric articulating trial component 120 of the trial assembly 12. The eccentric articulating trial component 120 may be compatible with the trial stem assembly 12 of FIGS. 2-8. The trial stem assembly 12 may include the distal stem 16 to which the proximal neck component 16 may be pivotally secured by, for example, screw or fastener 18.

Figure 15:
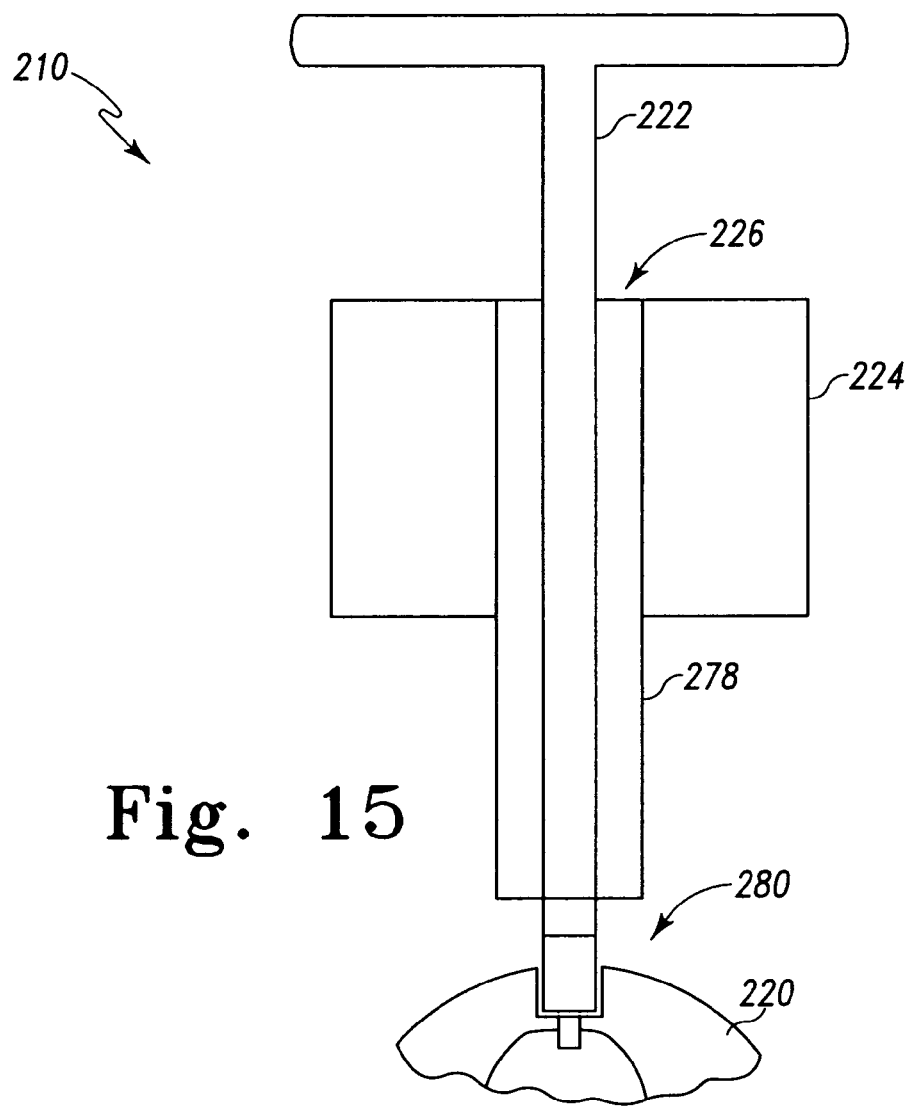
FIG. 15 is a partial plan view partially in cross section view of another embodiment of the present invention in the form of a kit with a driver and humeral head having a different connection to secure the head to the stem.
Figure 16:
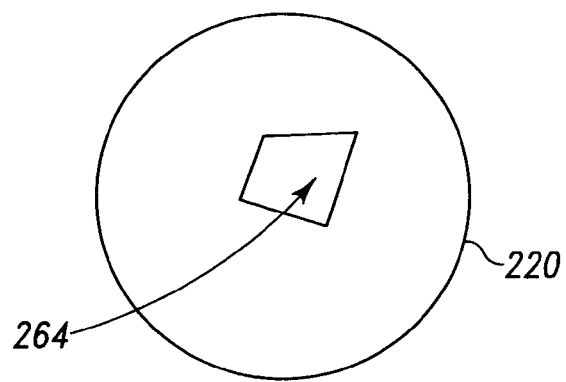
FIG. 16 is a top view of the humeral head of the kit of FIG. 15.
Figure 16A:
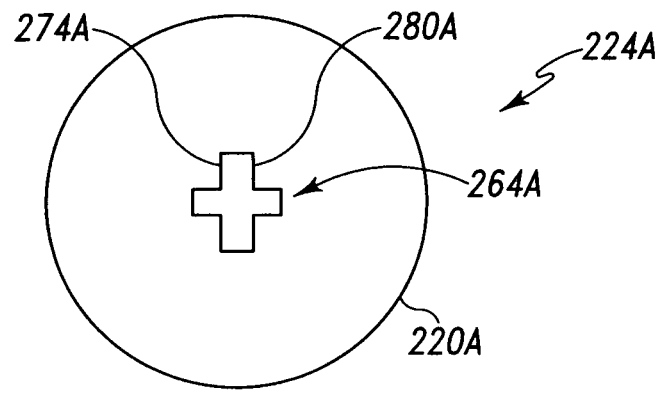
FIG. 16A is a top view of the humeral head of another embodiment of the present invention in the form of a kit with different shaped connection to secure the head to the stem.

Referring now to FIGS. 15 and 16 yet another embodiment of the present invention is shown as kit 210. The kit 210 may include the trial stem assembly 12. The trial stem assembly 12 may include the distal stem 16 to which the proximal neck component 16 may be pivotally secured by, for example, screw or fastener 18. The kit 210 includes an articulating trial component 220 that is different than the articulating trial component 20 of FIGS. 1-8 in that the articulating trial component 220 includes a first cavity 264 that has an orientation feature that eliminates the need for a second cavity.

The kit 210 may include a handle 224 with a connector 280 extending outwardly from shaft 278 of handle 224. The connector 280 cooperates with first cavity 264 to orient component 220. A driver 222 which may slideably fit through opening 226 formed in handle 224. The driver 222 may for example have a four sided odd shape to mate with the portion of the articulating trial component 220 that forms first cavity 264.

Referring now to 16A, yet another embodiment of the present invention is shown as handle 224A. The handle 224A includes a connector 280A extending outwardly from shaft 274A of the handle 224A. The connector 280A has an X-shape that mates with the X-shape of opening 264 formed on articulating trial component 220A.

Figure 16B:
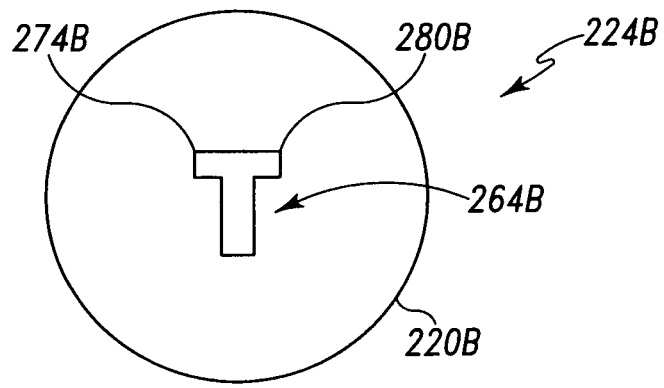
FIG. 16B is a top view of the humeral head of another embodiment of the present invention in the form of a kit with different shaped connection to secure the head to the stem.

Referring now to FIG. 16B, yet another embodiment of the present invention is shown as handle 224B. The handle 224B includes a connector 280B extending from an end of the shaft portion 274B of the handle 224B. The connector 280B has a generally T-shape that mates with the T-shape of opening 264 formed in articulating trial component 220B.

Figure 16C:
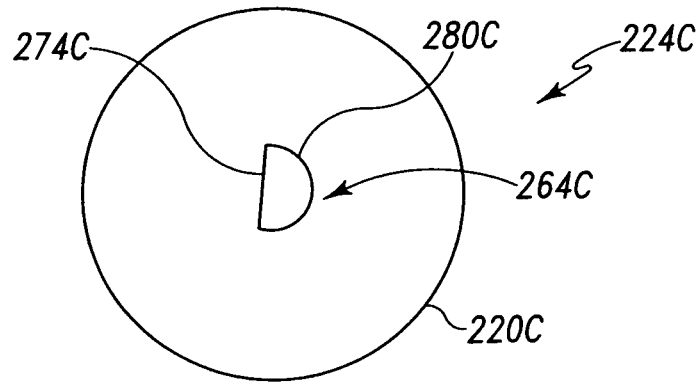
FIG. 16C is a top view of the humeral head of another embodiment of the present invention in the form of a kit with different shaped connection to secure the head to the stem.

Referring now to FIG. 16C, yet another embodiment of the present invention is shown as handle 224C. The handle 224C has a connector 280C extending from an end of the shaft 274C of the handle 224C that is circular with a flat on one side. The connector 280C mates with an opening 264C having a similar shape and extending from the articulating trial component 220C.

Figure 16D:
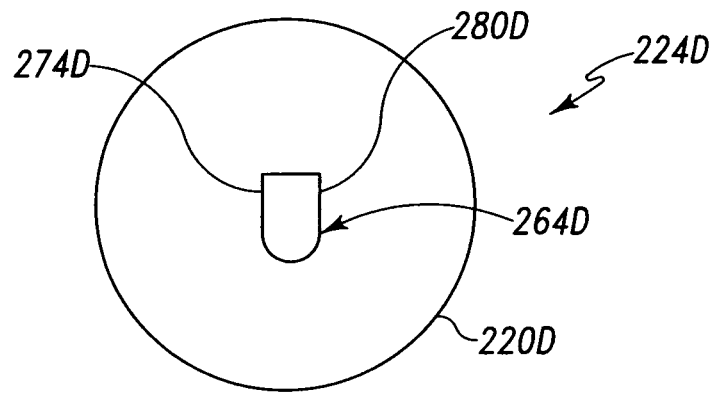
FIG. 16D is a top view of the humeral head of another embodiment of the present invention in the form of a kit with different shaped connection to secure the head to the stem.

Referring now to FIG. 16D, yet another embodiment of the present invention is shown as handle 224D. The handle 224D includes a connector 280D extending from an end of shaft 274D of the handle 224D. The connector 280D has a generally U-shaped configuration and mates with the U-shaped configuration of opening 264D formed in articulating trial component 220D.

Figure 16E:
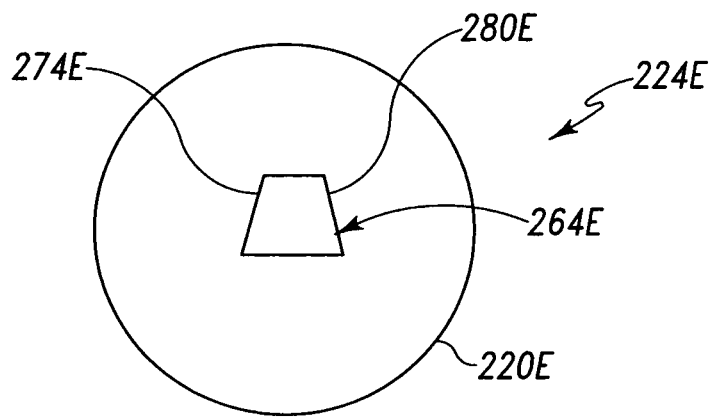
FIG. 16E is a top view of the humeral head of another embodiment of the present invention in the form of a kit with different shaped connection to secure the head to the stem.

Referring now to FIG. 16E, yet another embodiment of the present invention is shown as handle 224E. The handle 224E includes a connector 280E which extends from an end of the shaft 274E of the handle 224E. The connector 280E has a generally isosceles triangle shape and mates with an isosceles triangle shape of a hole 264E formed in articulating trail component 220E.

Although the present invention and its advantages have been described in detail, it should be understood that various changes, substitutions, and alterations can be made therein without departing from the spirit and scope of the present invention as definite by the appended claims.

We claim:

1. A kit for use in performing a trial reduction in joint arthroplasty, said kit comprising:
   a trial stem assembly including a first component, a second component selectably moveable with respect to the first component, and a fastener configured to engage the second component to secure the first component to the second component;
   an articulating trial component configured to be secured to said second component;
   a driver having a longitudinal portion with a fastener engaging portion at an end thereof, said fastener engaging portion configured to cooperate with the fastener to secure the first component to the second component; and
   a handle having (i) a longitudinal passageway configured to permit said fastener engaging portion of the driver to be freely passed through and removed from said longitudinal passageway, and (ii) a mating feature configured to mate with a complementary structure defined in said articulating trial component.

2. The kit of claim 1, wherein the first component, the second component and the fastener are configured such that in a first mode the first component of said trial stem assembly is secured to the second component of said trial stem assembly in a manner that enables said second component to be pivoted and rotated with respect to the first component, and in a second mode the first component of said trial stem assembly is secured to the second component of said trial stem assembly in a manner that prohibits said second component from being pivoted and rotated with respect to the first component.

3. The kit of claim 1, wherein said articulating trial component has an articulating surface, the articulating surface being one of concave and convex.

4. The kit of claim 3, wherein said articulating surface is a truncated sphere.

5. The kit of claim 1:
   wherein said trial stem assembly is a humeral trial stem assembly; and
   wherein said articulating trial component is a humeral head.

6. The kit of claim 1:
   wherein the first component of said trial stem assembly comprises a humeral trial stem having a concave surface defining a cavity in the humeral trial stem; and
   wherein the second component of said humeral trial stem assembly comprises a humeral trial neck having a convex portion for cooperation with the concave surface of the humeral trial stem and having a stem for cooperation with said articulating trial component.

7. The kit of claim 1:
   wherein said handle defines a longitudinal axis thereof substantially parallel to said longitudinal passageway;
   wherein the mating feature of said handle comprises a first member extending from an end of said handle along the longitudinal axis of said handle and a second member spaced apart from and parallel to the first member; and
   wherein said longitudinal passageway extends through and is surrounded by said first member.

8. The kit of claim 7, wherein the first member and the second member have a cylindrical shape.

9. The kit of claim 7, wherein said complementary structure of said articulating trial component comprises:

a first internal wall defining a first cavity for receiving the first member of the mating feature of said handle; and a second internal wall defining a second cavity for receiving the second member of the mating feature of said handle.

10. A tool assembly for use in performing a trial reduction in joint arthroplasty using a trial stem assembly having a first component and second component connected by a fastener and having an articulation trial component, said tool assembly comprising:

a driver having a longitudinal portion with a fastener engaging portion at a distal end thereof, said fastener engaging portion for cooperation with the fastener to secure the first component to the second component; and a handle having (i) a longitudinal passageway defining an axis and configured to permit said fastener engaging portion of the driver to be freely passed through and removed from said longitudinal passageway of said handle, and (ii) a mating feature including a first member extending from an end portion of said handle along the axis of said passageway and a second member extending from the end portion of said handle and spaced apart from, and radially outwardly with respect to the axis from, the first member, each of the first member and the second member configured to mate with complementary structures defined in said articulating trial component, wherein said longitudinal passageway extends through and is surrounded by said first member, and the first member and the second member have a cylindrical shape.

11. The tool assembly of claim 10, wherein the first member and the second member are parallel with the passageway axis.

12. The tool assembly of claim 11, wherein the second member is longer than the first member.

13. The kit of claim 6, wherein the convex portion comprises at least one slot.

14. The kit of claim 13, wherein the second component further comprises:

a longitudinal opening extending from the stem to the convex portion, the longitudinal opening configured to receive the fastener.

15. The kit of claim 14, wherein:
the fastener includes a threaded portion; and
a portion of the longitudinal opening is threaded.

16. The kit of claim 6, wherein the convex portion is resilient.

17. The tool assembly of claim 10, wherein said first and second members are configured to mate with complementary structure defined in one of convex and concave surface.

18. The tool assembly of claim 17:
wherein said articulating trial component is a humeral head.

19. A tool assembly for use in performing a trial reduction in joint arthroplasty using a trial stem assembly having a first component and second component connected by a fastener and having an articulation trial component, said tool assembly comprising:

a driver having a longitudinal portion with a fastener engaging portion at a distal end thereof, said fastener engaging portion for cooperation with the fastener to secure the first component to the second component; and a handle having (i) a longitudinal passageway defining an axis and configured to permit said fastener engaging portion of the driver to be freely passed through and removed from said longitudinal passageway of said handle, and (ii) a mating feature including a first member extending from an end portion of said handle along the axis of said passageway and a second member extending from the end portion of said handle and spaced apart from the first member, each of the first member and the second member configured to mate with complementary structures defined in said articulating trial component, wherein a first minimum distance from the axis to the second member is greater than a second minimum distance from the axis to the first member.

20. The tool assembly of claim 19, wherein:
said first and second members are configured to mate with complementary structure defined in one of convex and concave surface,
wherein said articulating trial component is a humeral head, and
wherein said longitudinal passageway extends through and is surrounded by said first member.

* * * * *